United States Patent [19]

Freeburne et al.

[11] Patent Number: 5,312,948
[45] Date of Patent: May 17, 1994

[54] PARTICLE SIZE DISTRIBUTION FOR FLUIDIZED-BED PROCESS FOR MAKING ALKYLHALOSILANES

[75] Inventors: Steven K. Freeburne, Edgewood, Ky.; Roland L. Halm; Joseph P. Kohane, both of Madison, Ind.; Jonathan D. Wineland, Fareham, United Kingdom

[73] Assignee: Dow Corning Corporation, Midland, Mich.

[21] Appl. No.: 133,241

[22] Filed: Oct. 8, 1993

[51] Int. Cl.$^5$ ............................................. C07F 7/16
[52] U.S. Cl. ............................................. 556/472
[58] Field of Search ................................. 556/472

[56] References Cited

U.S. PATENT DOCUMENTS

| | | | |
|---|---|---|---|
| Re. 33,452 | 11/1990 | Ward et al. | 556/472 |
| 2,380,995 | 8/1945 | Rochow | 556/472 |
| 2,380,996 | 8/1945 | Rochow | 556/472 |
| 2,389,931 | 11/1945 | Reed et al. | 556/472 |
| 2,466,413 | 4/1949 | Gilliam et al. | 556/472 |
| 3,133,109 | 5/1964 | Dotson | 556/472 |
| 4,218,387 | 8/1980 | Maas et al. | 556/472 |
| 4,281,149 | 7/1981 | Shade | 556/472 |
| 4,307,242 | 12/1981 | Shah et al. | 556/472 |
| 4,554,370 | 11/1985 | Ward et al. | 556/472 |
| 5,015,751 | 5/1991 | Feldner et al. | 556/472 |
| 5,239,102 | 8/1993 | Webb et al. | 556/472 |
| 5,243,061 | 9/1993 | Webb et al. | 556/472 |
| 5,250,716 | 10/1993 | Mui | 556/472 |

*Primary Examiner*—Paul F. Shaver
*Attorney, Agent, or Firm*—William F. Boley

[57] ABSTRACT

The present invention is an improved process for the reaction of an alkyl halide with particulate silicon in a fluidized-bed process. The improvement comprises controlling the particle size of the silicon within a range of one micron to 85 microns. Preferred is when the particle size of the silicon has a mass distribution characterized by a 10th percentile of 2.1 to 6 microns, a 50th percentile of 10 to 25 microns, and a 90th percentile of 30 to 60 microns. Most preferred is when the particle size mass distribution of the silicon is characterized by a 10th percentile of 2.5 to 4.5 microns, a 50th percentile of 12 to 25 microns, and a 90th percentile of 35 to 45 microns. The process is run in the presence of a catalyst composition comprising copper and other catalysts.

10 Claims, No Drawings

PARTICLE SIZE DISTRIBUTION FOR FLUIDIZED-BED PROCESS FOR MAKING ALKYLHALOSILANES

BACKGROUND OF INVENTION

The present invention is an improved process for the reaction of an alkyl halide with particulate silicon in a fluidized-bed process. The improvement comprises controlling the particle size of the silicon within a range of one micron to 85 microns. Preferred is when the particle size of the silicon has a mass distribution characterized by a 10th percentile of 2.1 to 6 microns, a 50th percentile of 10 to 25 microns and a 90th percentile of 30 to 60 microns. Most preferred is when the particle size mass distribution of the silicon is characterized by a 10th percentile of 2.5 to 4.5, a 50th percentile of 12 to 25 microns, and a 90th percentile of 35 to 45 microns. The process is run in the presence of a catalyst composition comprising copper and other catalysts.

The present invention relates to an improvement of what is commonly referred to as the Direct Process for producing alkylhalosilanes, where the process comprises contacting an alkyl halide with particulate silicon in the presence of a copper catalyst. The process was first described by Rochow in U.S. Pat. No. 2,380,996 and U.S. Pat. No. 2,380,995, issued Aug. 7, 1945.

Since the original description of the Direct Process by Rochow, the process has been refined and modified in numerous ways and is used for producing virtually all commercial alkylhalosilanes in the world today. When one considers that several million pounds of silanes are produced annually and consumed by the silicones commercial effort, it is obvious why even small incremental increases in selectivity and raw material conversion are important to the manufacturer of alkylhalosilanes.

Commercially, the largest volume alkylhalosilane manufactured is dimethyldichlorosilane as this alkylhalosilane constitutes the backbone of most high volume commercial silicone products after it has been hydrolyzed and condensed to form silicone polymers. Therefore, it is to the benefit of the manufacture to run the Direct Process to maximize the conversion of the raw materials to obtain the highest yield of dialkyldihalosilane. Thus one of the objectives of the present invention is to control the Direct Process to maximize the overall yield of dialkyldihalosilane, i.e. to cause the process to be as selective as possible in favor of dialkyldihalosilane. A second objective of the present invention is to maximize the overall yield from the raw materials. The more of the raw materials that are converted to silanes, the more economical is the process. A third objective is to provide a process where less silicon spent bed of reduced activity in the process is produced.

The art has long recognized that in the Direct Process the size of the particulate silicon is important in determining the efficiency of the reaction of alkyl halides with silicon to form alkylhalosilanes. For the purpose of the present invention the efficiency of the reaction of alkyl halides with silicon is tracked by the amount of silicon charge that is converted to dialkyldihalosilane. However, the prior art has generally taught away from the optimal particle size range discovered and now disclosed by the present inventors.

Reed et al., U.S. Pat. No. 2,389,931, issued Nov. 27, 1945, first taught the use of a fluidized-bed of particulate silicon to conduct the Direct Process. Reed et al. taught that the silicon reactant should be in finely-divided or powdered form. By way of example. Reed et al. described the use of a sintered silicon-copper mixture crushed to 60–100 mesh (149 to 250 microns).

Gilliam et al., U.S. Pat. No. 2,466,413, issued Apr. 5, 1949, appear to be the first to report the effect of silicon particle size on performance of the Direct Process. Gilliam et al. reported that an optimal particle size for silicon in the Direct Process was a distribution where 100% of the particles are smaller than 420 microns in diameter, from 90 to 100% of the particles less than 149 microns in diameter and not more than 60% of the particles are less than 44 microns in diameter. Gilliam et al. used a packed-bed reactor to arrive at this optimal particle size distribution.

Dotson, U.S. Pat. No. 3,133,109, issued May 12, 1964, describes a process reported to be an improvement on Reed et al., supra. The improvement of Dotson being (1) adding to the fluidized bed make-up silicon having an average particle size greater than the average particle size of the silicon comprising the fluidized bed and (2) comminuting at least intermittently in a non-oxidizing atmosphere at least a portion of the silicon being adjusted to maintain a substantially constant average particle size for the silicon comprising the fluidized bed. Dotson teaches that for optimal results the silicon in the reactor should have an average particle diameter in the range of from about 20 to 200 microns. Dotson teaches preferably at least 25 percent by weight of the silicon particles have actual diameters in the range of from 20 to 200 microns.

Maas et al., U.S. Pat. No. 4,218,387, issued Aug. 19, 1980, describe a vibrating-bed type reactor for conducting the Direct Process on a laboratory scale. The silicon evaluated was reported to have a particle size distribution characterized as follows: $<36$ $\mu$m (31.3%): 36–71 $\mu$m: (22.6%): 71–100 $\mu$m: (17.8%): 100–160 $\mu$m: (18.0%): and $>160$ $\mu$m (10.3%).

Shade, U.S. Pat. No. 4,281,149, issued Jul. 28, 1981, describes a process for extending the activity of a fluidized bed used in the Direct Process. The process described by Shade consists of removing particles selected from particles of silicon and copper of less than 40 microns average diameter size from the reactor and abrading said particles to remove the surface coating of such particles and returning the particles to the reactor. Shade teaches that for optimal results the silicon in the reactor has an average particle diameter in the range of from about 20 to 200 microns. Preferably at least 25 percent by weight of the silicon particles have actual diameters in the range of from 20 to 200 microns.

Shah et al., U.S. Pat. No. 4,307,242, issued Dec. 22, 1981, also report a fluidized-bed Direct process where the silicon in the reactor has an average particle diameter in the range of from about 20 to 200 microns. Preferably at least 25 percent by weight of the silicon particles have actual diameters in the range of from 20 to 200 microns.

Ward et al., U.S. Pat. No. 4,554,370, issued Nov. 19, 1985, teach the use of fumed silica in a mixture of powdered silicon and cuprous chloride to reduce agglomeration in a fluidized-bed reactor during conduct of the Direct Process. Ward et al. teach that the silicon present in the fluidized bed can have a particle size below 700 microns, with an average particle size of greater than 20 microns and less than 300 microns in size. The mean diameter of the silicon particles is preferably in the range of 100 to 150 microns.

Ward et al., U.S. Pat. No. Re. 33,452, issued Nov. 20, 1990, teach the use of a copper-zinc-tin catalyst in the direct process. Ward et al. teach that significant improvements in reaction rate and product selectivity are achieved when copper is employed at a critical weight percent relative to silicon and critical weight ratios of tin and zinc are employed relative to copper. Ward et al. teach that the process can be conducted in a fluidized-bed using silicon having a particle size below 700 microns, with an average size of greater than 20 microns and less than 300 microns in size. The mean diameter of the silicon particles is preferably in the range of 100 to 150 microns.

In view of the cited art, quite unexpectly the present inventors have found that the optimal silicon particle size for conducting the Direct Process in a fluidized-bed reactor is within a range of about one micron to 85 micron. Preferred is when the particle size of the silicon has a mass distribution characterized by a 10th percentile of 2.1 to 6 microns, a 50th percentile of 10 to 25 microns, and a 90th percentile of 30 to 60 microns. Most preferred is when the particle size mass distribution of the silicon is characterized by a 10th percentile of 2.5 to 4.5, a 50th percentile of 12 to 25 microns, and a 90th percentile of 35 to 45 microns. The inventors have discovered that particles outside of the described ranges degrade the efficiency of the reactor and therefore it is preferable that these sizes of particles not be added to the reactor or if added be controlled within defined mass ranges.

SUMMARY OF INVENTION

The present invention is an improved process for the reaction of an alkyl halide with particulate silicon in a fluidized-bed process. The improvement comprises controlling the particle size of the silicon within a range of one micron to 85 microns. Preferred is when the particle size of the silicon has a mass distribution characterized by a 10th percentile of 2.1 to 6 microns, a 50th percentile of 10 to 25 microns, and a 90th percentile of 30 to 60 microns. Most preferred is when the particle size mass distribution of the silicon is characterized by a 10th percentile of 2.5 to 4.5 microns, a 50th percentile of 12 to 25 microns, and a 90th percentile of 35 to 45 microns. The process is run in the presence of a catalyst composition comprising copper and other catalysts.

DESCRIPTION OF INVENTION

The present invention is a process for the manufacture of alkylhalosilanes described by formula

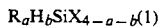
$$R_aH_bSiX_{4-a-b} \quad (1)$$

The process comprises: contacting an alkyl halide described by formula

$$RX \quad (2)$$

with a fluidized-bed of particulate silicon where the particulate silicon has a size within a range of about one micron to 85 microns in the presence of a catalyst composition comprising copper, at a temperature within a range of about 250° C. to 350° C.; where each R is independently selected from a group consisting of alkyls comprising one to four carbon atoms; a=0, 1, 2, 3, or 4; b=0, 1, 2, or 3; a+b=1, 2, 3 or 4; and X is a halogen.

The alkylhalosilanes which can be manufactured by the present invention are those described by formula (1). In formula (1) each R is independently selected from a group consisting of alkyls comprising one to four carbon atoms. The substituent R can be, for example, methyl, ethyl, propyl, isopropyl, butyl, and tert-butyl. In formula (1) the term a can have a value of zero, one, two, three, or four; the term b can have a value of zero, one, or two; and the sum of terms a and b can be one, two, three, or four. The preferred alkylhalosilanes are those having the formula $R_2SiX_2$, where R is methyl or ethyl and X is chlorine. The most preferred alkylhalosilane is dimethyldichlorosilane, i.e. $(CH_3)_2SiCl_2$.

In the present process an alkyl halide is contacted with particulate silicon. Alkyl halides useful in the present process are described by formula (2), where R is as previously described and X is a halogen. Preferred is when X is the chlorine atom. The preferred alkyl halide is methyl chloride.

Contact of the alkyl halide with the particulate silicon is effected in a fluidized-bed of the particulate silicon. The process can be conducted in standard type reactors for reacting a fluidized-bed of particulates with a gas. The bed can be fluidized using the alkyl halide as the fluidizing media or using a mixture of the alkyl halide with a gas inert in the process as the fluidizing media.

The present inventors have discovered that for optimal efficiency of the process the particulate silicon must have a closely defined particle size or particle size distribution which has not previously been recognized in the art. For purposes of the present invention process efficiency is defined as the percent of silicon converted to dialkyldihalosilane. Process efficiency is a function of the process specificity for the dialkyldihalosilane, amount of silicon converted to monosilanes, and of the amount of silicon converted per unit time.

The reaction of alkyl halides with particulate silicon is known to be a surface reaction. Alkyl halides react with silicon on catalytically activated silicon surfaces. More available silicon surface gives more potential for reaction in a given volume, so reaction rate is related to the specific surface area of particles available. Smaller particles have high specific surface areas and react away quickly while larger particles have a lower specific surface area and a corresponding lower reaction rate. Furthermore since the silicon particles spend a finite residence time in the reactor, faster reacting small particles are more likely to be consumed to give high silicon conversion and consequently less silicon spent bed.

However, the present inventors have found that below the particulate silicon size limits described herein process efficiency is lost. The inventors believe that when the particle size becomes too small or when the particle size distribution contains too large of a mass of particles below the defined ranges interparticle forces cause the fluidizing gases to "bypass" or "channel" through the fluidized bed. This "bypassing" or channeling" gives poorer solids mixing and heat transfer properties within the fluidized bed.

Therefore, the inventors have found that it is desirable to have a silicon particle size for the present process within a range of about one micron to 150 micron. A preferred silicon particle size is within a range of about one micron to 85 micron. A more preferred silicon particle size is within a range of about two to 50 microns. It is preferred that the silicon have a particle size mass distribution characterized by a 10th percentile of 2.1 to 6 microns, a 50th percentile of 10 to 25 microns, and a 90th percentile of 30 to 60 microns. Most preferred is when the particle size mass distribution of the silicon is characterized by a 10th percentile of 2.5 to 4.5 microns, a 50th percentile of 12 to 25 microns, and a 90th percentile of 35 to 45 microns.

The described distributions are characterized by three percentile sizes. Each percentile describes the particle size in microns below which a mass percentage of the size distribution resides: i.e. "10th percentile" - 10 percent of the mass distribution is smaller than the 10th percentile size: "50th percentile" - 50 percent of the mass distribution is smaller than the 50th percentile size: and "90th percentile" - 90 percent of the mass distribution is smaller then the 90th percentile size.

The method of making the particle size distributions useful in the present process is not critical. Standard methods for producing particulate silicon can be used, for example, the use of a roller or ball mill to grind silicon lumps. The powdered silicon may be further classified as to particle size distribution by means of, for example, screening or use of mechanical classifiers such as a rotating classifier.

The present process is conducted in the presence of a catalyst composition comprising copper. The present process requires the presence of copper as a catalyst within a range of about 0.1 to 10 weight percent of the silicon present in the process. The source of the copper added to the process may be powdered copper metal, powdered silicon-copper alloy, a compound of copper, or a mixture of two or more sources of copper. The copper compound may be, for example, cuprous chloride.

In addition to copper, the catalyst composition may employ other metals as catalysts. The scope of other metals contemplated as catalysts by the inventors are those metals known to those skilled in the art as promoters of the Direct Process. Examples of such catalytic metals are described by and incorporated by reference herein, Halm et al., U.S. Pat. No. 4,602,101, issued Jul. 22, 1986; Halm et al., U.S. Pat. No. 4,946,978, issued Aug. 7, 1990: Halm et al., U.S. Pat. No. 4,762,940, issued Aug. 9, 1988: and Ward et al., U.S. Pat. No. Re. 33,452, issued Nov. 20, 1990. These catalytic metals include, for example, phosphorous, phosphorous compounds, zinc, zinc compounds, tin, tin compounds, and mixtures thereof.

A preferred catalyst composition for the present process comprises on an elemental basis by weight: 0.1 to 10 weight percent copper based on silicon present in the process, 50 to 10,000 ppm zinc, 5 to 200 ppm tin, and 25 to 2,500 ppm phosphorous.

The process can be conducted at a temperature within a range of about 250° C. to 350° C. The preferred temperature for conducting the present process is within a range of about 270° C. to 320° C.

The following examples are offered to illustrate the present invention. These examples are not intended to limit the scope of the present claims.

EXAMPLE 1

(Not within the scope of the present invention.)

A control baseline for the reaction of metallurgical grade silicon with methyl chloride was established. A mixture comprising 100 parts of refined, ground metallurgical grade silicon (aluminum=0.16 Wt. %, iron=0.32 Wt. %, and calcium=0.004 Wt. %). 6.5 parts of cuprous chloride, 600 ppm brass (50 Wt. % zinc). 36 ppm tin, and 2000 ppm copper phosphorus alloy, was formed. The particle size mass distribution of the silicon was characterized as a 10th percentile of 2.8μ, a 50th percentile of 22μ, and a 90th percentile of 81μ.

The mixture was charged to a reactor similar to that described by Mass et al., U.S. Pat. No. 4,218,387, issued Aug. 19, 1980. The temperature of the reactor was maintained at about 315° C. by means of a constant temperature bath. The reactor was purged for 15 minutes with nitrogen gas. The nitrogen purge was then shut off and methyl chloride gas was fed to the reactor for a total of 44 hours during which time all products and unreacted methyl chloride were collected in a cold-trap. Weight loss of the reactor was used as an indicator of silicon conversion. The liquid collected in the cold-trap was analyzed by gas chromotography (GC) using a thermal conductivity (TC) detector. The performance of the silicon in each run was calculated as the weight fraction of silicon consumed times the weight percent of dimethyldichlorosilane as a percent of the total weight of silane products formed. The average silicon performance for this series of runs was determined to be 77.9 percent.

EXAMPLE 2

Samples of particulate metallurgical grade silicon having various particle size mass distributions were evaluated in a process similar to that described in Example 1. The specific particle size mass distribution and silicon performance is provided in Table 1. Each sample of a specific particle size mass distribution was run in duplicate and the average silicon performance for the two runs is reported in Table 1 under the heading "Si-Perf." The 10th, and 90th percentile particle mass distributions where determined by use of a Micromeritics Sedigraph Model 5000. The sieve mesh size that the silicon powder passed is also indicated in Table 1. Results were analyzed and silicon performance calculated as described in Example 1.

TABLE 1

| Silicon Particle Size Distribution Effects on Performance | | | | | |
|---|---|---|---|---|---|
| Sample No. | Particle Mass Distribution (μ) | | | Mesh | Si-Perf. |
| | 10th | 50th | 90th | | |
| 1 | 2.2 | 13.0 | 36.5 | <325 | 81.9 |
| 2 | 1.6 | 10.7 | 35.0 | <325 | 67.8 |
| 3 | 1.7 | 10.2 | 31.0 | <325 | 69.1 |
| 4 | 2.4 | 15.7 | 49.0 | <230 | 80.4 |
| 5 | 2.2 | 14.0 | 40.5 | <270 | 84.2 |
| 6 | 2.4 | 13.5 | 41.1 | <325 | 83.1 |
| 7 | 2.0 | 11.2 | 32.3 | <400 | 75.8 |

We claim:

1. A process for the manufacture of alkylhalosilanes described by formula $$R_aH_bSiX_{4-a-b}$$

the process comprising: contacting an alkyl halide described by formula $$RX$$

with a fluidized-bed of particulate silicon where the particle silicon has a size within a range of about one micron to 85 microns in the presence of a catalyst composition comprising copper, at a temperature within a range of about 250° C. to 350° C.;

where each R is independently selected from a group consisting of alkyls comprising one to four carbon atoms; a=1, 2, 3, or 4; b=0, 1, or 2; a+b=1, 2, 3, or 4; and X is a halogen.

2. A process according to claim 1, where the particulate silicon has a particle size mass distribution characterized by a 10th percentile of 2.1 to 6 microns, a 50th percentile of 10 to 25 microns, and a 90th percentile of 30 to 60 microns.

3. A process according to claim 1, where the particulate silicon has a particle size mass distribution characterized by a 10th percentile of 2.5 to 4.5 microns, a 50th percentile of 12 to 25 microns, and a 90th percentile of 35 to 45 microns.

4. A process according to claim 1, where the alkyl halide is methyl chloride.

5. A process according to claim 1, where the catalyst composition comprises on an elemental basis by weight: 0.1 to 10 weight percent copper based on the silicon present in the process, 50 to 10,000 ppm zinc, 5 to 200 ppm tin, and 25 to 2.500 ppm phosphorous.

6. A process according to claim 1, where the temperature is within a range of about 270° C. to 320° C.

7. A process according to claim 1, where the alkylhalosilane is dimethyldichlorosilane.

8. A process according to claim 1, where the alkyl halide is methyl chloride; the catalyst composition comprises on an elemental basis, by weight, 0.1 to 10 weight percent copper based on silicon present in the process, 50 to 10,000 ppm zinc, 5 to 200 ppm tin, and 25 to 2,500 ppm phosphorous; and the temperature is within a range of about 270° C. to 320° C.

9. A process according to claim 2 where the alkyl halide is methyl chloride; the catalyst composition comprises on an elemental basis, by weight, 0.1 to 10 weight percent copper based on silicon present in the process, 50 to 10,000 ppm zinc, 5 to 200 ppm tin, and 25 to 2,500 ppm phosphorous; and the temperature is within a range of about 270° C. to 320° C.

10. A process for the manufacture of alkylchlorosilanes described by formula $$R_a H_b SiCl_{4-a-b}$$

where R is an alkyl radical comprising one to four carbon atoms; a=1, 2, 3, or 4; b=0, 1, or 2; a+b=1, 2, 3, or 4; the process comprising: charging 100 parts by weight particulate silicon to a fluidized-bed reactor, the particulate silicon consisting essentially of particles within a size range of about 1 micron to 85 microns, adding 0.1 to 10 parts by weight of a catalyst composition comprising copper to the particulate silicon in the fluidized-bed reactor, and contacting an alkylchloride described by formula $$RCl$$

with the particulate silicon and the catalyst composition in the fluidized-bed reactor at a temperature within a range of about 250° C. to 350° C.

* * * * *